US007022712B2

(12) United States Patent
Yalkowsky (10) Patent No.: US 7,022,712 B2
(45) Date of Patent: Apr. 4, 2006

(54) SOLUBILIZATION OF WEAK BASES (75) Inventor: Samuel H. Yalkowsky, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 10/402,347

(22) Filed: Mar. 26, 2003

(65) Prior Publication Data
US 2003/0195225 A1 Oct. 16, 2003

Related U.S. Application Data (60) Provisional application No. 60/368,684, filed on Mar. 26, 2002.

(51) Int. Cl.
A61K 31/4745 (2006.01)
A61K 31/4196 (2006.01)

(52) U.S. Cl. .............. 514/303; 514/322; 514/394; 546/118; 546/199

(58) Field of Classification Search ........... 548/335.1, 548/312.1; 514/394, 396, 395, 338, 303, 514/322; 546/268.1, 268.7, 269.1, 269.7, 546/118, 199
See application file for complete search history.

(56) References Cited

U.S. PATENT DOCUMENTS

| 3,738,995 | A |   | 6/1973  | Adams et al. ........... 260/309.2 |
| 3,954,993 | A | * | 5/1976  | Pommer et al. ............. 514/533 |
| 4,405,605 | A |   | 9/1983  | Itzel ............................ 424/173 |
| 4,550,174 | A |   | 10/1985 | Köch et al. ................... 548/306 |
| 4,593,040 | A |   | 6/1986  | Adam et al. ................. 514/395 |
| 4,835,169 | A |   | 5/1989  | Wiedmer ..................... 514/383 |
| 4,980,346 | A |   | 12/1990 | Balogh et al. ............... 514/118 |
| 5,124,353 | A |   | 6/1992  | Clough et al. .............. 514/510 |
| 5,198,444 | A |   | 3/1993  | Clough et al. .............. 514/269 |
| 5,252,321 | A |   | 10/1993 | Hth et al. ................. 424/78.32 |
| 5,629,341 | A |   | 5/1997  | Camden |
| 5,723,648 | A |   | 3/1998  | Ueda |
| 5,756,500 | A |   | 5/1998  | Beilfuss et al. ............. 514/245 |
| 5,767,138 | A |   | 6/1998  | Camden ..................... 514/365 |
| 5,880,144 | A |   | 3/1999  | Camden ..................... 514/397 |
| 6,077,862 | A |   | 6/2000  | Camden |
| 6,194,430 | B1 | * | 2/2001  | Camden et al. ............. 514/303 |
| 6,197,805 | B1 |   | 3/2001  | Smith ........................ 514/388 |
| 6,228,400 | B1 |   | 5/2001  | Lee et al. ................... 424/489 |
| 6,245,789 | B1 |   | 6/2001  | Camden ..................... 514/365 |
| 6,262,093 | B1 |   | 7/2001  | Camden |
| 6,265,427 | B1 |   | 7/2001  | Camden ..................... 514/388 |
| 6,331,320 | B1 |   | 12/2001 | Nakahara et al. ........... 424/725 |
| 6,362,207 | B1 |   | 3/2002  | Camden ..................... 514/365 |
| 6,380,232 | B1 |   | 4/2002  | Quada, Jr. |
| 6,384,049 | B1 |   | 5/2002  | Camden |
| 6,407,105 | B1 |   | 6/2002  | Quada, Jr. |
| 6,407,131 | B1 |   | 6/2002  | Quada, Jr. |
| 6,413,973 | B1 |   | 7/2002  | Walter et al. ............... 514/259 |
| 6,420,411 | B1 |   | 7/2002  | Camden |
| 6,423,734 | B1 |   | 7/2002  | Camden |
| 6,423,735 | B1 |   | 7/2002  | Camden |
| 6,423,736 | B1 |   | 7/2002  | Camden |
| 6,432,965 | B1 |   | 8/2002  | Müller et al. ............... 514/258 |
| 6,462,062 | B1 |   | 10/2002 | Camden |
| 6,479,526 | B1 | * | 11/2002 | Camden ..................... 514/365 |
| 6,482,843 | B1 |   | 11/2002 | Quada, Jr. |
| 6,506,783 | B1 |   | 1/2003  | Camden |
| 6,608,096 | B1 |   | 8/2003  | Camden |
| 6,710,065 | B1 |   | 3/2004  | Camden |
| 2001/0027205 | A1 |   | 10/2001 | Camden |
| 2002/0193609 | A1 |   | 12/2002 | Quada, Jr. |

FOREIGN PATENT DOCUMENTS

| EP | EP 0821586   | 2/1998  |
| WO | WO 98/51304  | 11/1998 |
| WO | WO 01/12169 A2 | 2/2001 |
| WO | WO 01/89499 A2 | 11/2001 |
| WO | WO 01/12169 A3 | 2/2002 |
| WO | WO 02/26716 A2 | 4/2002 |
| WO | WO 02/41891 A2 | 5/2002 |
| WO | WO 01/89499 A3 | 7/2002 |
| WO | WO 02/26716 A3 | 7/2002 |
| WO | WO 02/41891 A3 | 5/2003 |

OTHER PUBLICATIONS

Monika et. al., "Combined chromatographic techniques in pesticide residue analysis", STN Search p. 8, 2003:381543.*
Solov'eva et al. "Effect of pH on fungicidal . . . " CA 87:112846 (1977).*
Burzi et al. "High pressure . . . " CA 95:78566 (1981).*

(Continued)

Primary Examiner—Celia Chang
(74) Attorney, Agent, or Firm—Greenlee, Winner and Sullivan, P.C.

(57) ABSTRACT

A pharmaceutical composition for administration to mammals comprising: a weak base compound having a compound pKa below about 7; an acidic buffer with a buffer pKa below 7; and optional pharmaceutically acceptable additives, wherein the composition has a pH below about 4 is provided. Preferred pharmaceutically active compounds are imidazole derivatives, pyridine derivatives, and aniline derivatives. The pharmaceutical compositions have greater water solubility than the weak base.

24 Claims, 10 Drawing Sheets

OTHER PUBLICATIONS

Singh et al. "Solubility of benomyl . . . " Ca 102:57632 (1985).* carbendazim CAS RN 10605-21-7.*

Nagano et al. "Improvement of solubility of benzimidazole preparations" CA 106:133842 (1987).*

Itzel "Fungicide mixtures" Ca 95:127461 (1981).*

H. Brown et al., *Antiparasitic Drugs. IV. 2-(4'-Thiazolyl)-Benzimidazole, A New Anthelmintic*, J. Am. Chem. Soc. 83:1764-1765, 1961.

S. Budavari, editor, *The Merck Index*, Merck & Co., New Jersey, Twelfth Edition, p. 291, 1996.

M. El-Sayed et al., *Combined Effect of pH Control with Surfactants or Complexants on 2-(4'-amino-3'-Methylphenyl) Benzothiazole (NSC-674495) Solubilization*, Bull. Fac. Pharm. Cairo Univ. 38(2):51-56, 2000.

V. Grenda et al., *Novel Preparation of Benzimidazoles from N-Arylamidines. New Synthesis of Thiabendazole*, J. Org. Chem. 30:259-261, 1965.

N. Ni et al., *Solubilization and Preformulation of Carbendazim*, Int. J. Pharmaceutics 244:99-104, Sep. 2002.

Remington, *Pharmaceutical Sciences*, Mack Publishing Co., Easton, Pa, 17$^{th}$ Edition, p. 1418, 1985.

S. Yalkowsky, *Solubility and Solubilization in Aqueous Media*, Oxford University Press, Oxford, pp 116-396, 1999.

\* cited by examiner

SOLUBILIZATION OF WEAK BASES

CROSS-REFERENCE TO RELATED APPLICATIONS

This application claims the benefit of U.S. Provisional Application Ser. No. 60/368,684, filed Mar. 26, 2002, which is hereby incorporated by reference to the extent not inconsistent with the disclosure herewith.

BACKGROUND OF THE INVENTION

This invention is in the field of improving the water solubility of benzimidazole derivatives and other weak bases and providing pharmaceutical formulations of the same. Benzimidazole derivatives are useful for inhibiting the growth of cancers, tumors and viruses in mammals, particularly in humans and warm-blooded animals (U.S. Pat. Nos. 6,479,526; 5,880,144; 6,245,789; 5,767,138; 6,265,437). Certain benzimidazole derivatives used in combination with other compounds have been reported to be useful as fungicides (U.S. Pat. Nos. 3,954,993; 4,593,040; 5,756,500; 4,835,169; 4,980,346). However, benzimidazole derivatives, including carbendazim, are poorly water soluble. The projected oral dose of carbendazim for cancer treatment is up to several hundred mg per day which is far greater than its water solubility. Other weak bases suffer from the same lack of water solubility.

A method of improving the water solubility of benzimidazole derivatives and other weak bases and pharmaceutical formulations of the same is needed.

BRIEF SUMMARY OF THE INVENTION

Provided are compositions of weak bases having greater water solubility than the weak bases alone. More specifically, provided are compositions comprising a weak base having a pKa below about 7; an acidic buffer having a buffer pKa below about 7; and optional pharmaceutically acceptable additives, wherein the composition has a pH below about 5. Also provided are methods of increasing the water solubility of a weak base, comprising: contacting the weak base with an acidic buffer, and optionally adding one or more pharmaceutically acceptable additives. Also provided are pharmaceutical compositions of weak bases. Particular pharmaceutical compositions are suitable for administration to mammals comprising: a pharmaceutically active weak base compound having a compound pKa below about 7; an acidic buffer having a buffer pKa below about 7; and optional pharmaceutically acceptable additives, wherein the composition has a pH below about 5.

As used herein, "weak base" or "weak bases" are those compounds having a pKa below about 7. Weak bases include prodrugs and salts of weak bases and salts of prodrugs. Preferred weak bases have a pKa below about 5. Other preferred weak bases have a pKa below about 4. Weak bases having pKa values below about 7 and compounds in all pKa ranges below about 7 are included in the invention. Some classes of weak bases include: imidazole derivatives having a pKa below about 7, pyridine derivatives having a pKa below about 7, aniline derivatives having a pKa below about 7 and compounds containing combinations thereof having a pKa below about 7. Imidazole derivatives are defined as compounds which include the structure:

Some preferred imidazole derivatives include the following:

| Compound | pKa |
| --- | --- |
| Cimetadine | 6.8 |

![Cimetadine structure with R = CN]

R = CN

| Glyodin | ~7 |

![Glyodin structure]

R = C17H25

| Miconazole | 6.7 |

![Miconazole structure]

Pyridine derivatives are defined as compounds which include the structure:

Some preferred pyridine derivatives include the following:

| Compound | pKa |
| --- | --- |
| Nicotinamide | 3.4 |

| Compound | pKa |
|---|---|
| Nikethamide  | 3.5 |

Aniline derivatives are defined as compounds which include the structure:

where R is hydrogen or alkyl having from 1 to 7 carbon atoms. The aromatic ring may have other substituents, as known in the art.

Some preferred aniline derivatives include the following:

| Compound | pKa |
|---|---|
| BPU NSC 639829  | ~5 |
| AMPB  | 4 |
| Minioxadil  | 4.6 |
| Benzocaione <br> $H_2N$—⌬—C(O)—O—CH$_2$CH$_3$ | 2.5 |

| Compound | pKa |
|---|---|
| Butamben  | 5.4 |

One class of imidazole derivatives include those with the formula:

where n is an integer from 1 to 3, R is hydrogen, alkyl having from 1 to 7 carbon atoms, chloro, bromo, fluoro, oxychloro, hydroxy, sulflhydryl, or alkoxy having the formula —$O(CH_2)_y(CH_3)$, wherein y is an integer from 0 to 6. One particular compound of this class is PG 300995:

Another class of imidazole derivatives includes benzimidazoles and benzimidazole derivatives. As used herein, "benzimidazoles" are those having the formula:

wherein X is hydrogen, halogen, alkyl of less than 7 carbon atoms or alkoxy of less than 7 carbon atoms; n is a positive integer of less than 4; Y is hydrogen, chlorine, nitro, methyl, ethyl or oxychloro; R is hydrogen, alkylaminocarbonyl wherein the alkyl group has from 3 to 6 carbon atoms or an alkyl group having from 1 to 8 carbons and $R_2$ is 4-thiazolyl, $NHCOOR_1$ wherein $R_1$ is aliphatic hydrocarbon of less than 7 carbon atoms, or an alkyl group of less than 7 carbon atoms. A preferred class of benzimidazoles are those wherein R is hydrogen. Another preferred class of benzimidazoles are:

wherein R is an alkyl of 1 through 8 carbon atoms and $R_2$ is selected from the group consisting of 4-thiazolyl or $NHCOOR_1$ wherein $R_1$ is methyl, ethyl or isopropyl and pharmaceutically acceptable acid salts thereof with both organic and inorganic acids.

As used herein, "benzimidazole derivatives" include benzimidazoles as defined above, prodrugs and salts of benzimidazoles and salts of prodrugs. "Prod rugs" are considered to be any covalently bonded carriers which release the active parent drug (weak base) according to the formula of the parent drug described above in vivo when such prodrug is administered to a mammalian subject. Prodrugs of the weak bases are prepared by modifying functional groups present in the compounds in such a way that the modifications are cleaved, either in routine manipulation or in vivo, to the parent compounds. Prodrugs include compounds wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate, or benzoate derivatives of alcohol and amine functional groups in the weak bases; phosphate esters, dimethylglycine esters, aminoalkylbenzyl esters, aminoalkyl esters and carboxyalkyl esters of alcohol and phenol functional groups in the weak bases; and the like.

Salts of benzimidazole derivatives and other weak bases include pharmaceutically acceptable salts. Pharmaceutically acceptable salts of the weak bases include the conventional salts or the quaternary ammonium salts of the weak bases formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The salts of the weak bases are synthesized from the weak bases which contain a basic or acidic moiety by conventional chemical methods. Generally, such salts are prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, for example, the disclosure of which reference is hereby incorporated by reference.

The compositions of the invention are useful for administration to animals, preferably mammals, and preferably humans. The compositions of the invention are administered using any form of administration and any suitable dosage that provides a pharmaceutically active dose in an animal, preferably a mammal, as known in the art. Preferably, the compositions of the invention are used for oral, slow intravenous injection or infusion administration, as known in the art. Because the compositions are acidic, other forms of administration may be unsuitable. If the compositions are injected, the injection speed should be slow to avoid local irritation, as known in the art.

"Pharmaceutically acceptable" and "non-toxic" mean suitable for use with humans and/or animals without undue adverse side effects (such as toxicity, irritation and allergic response) commensurate with a reasonable benefit/risk ratio. "Pharmaceutically active" means capable of causing an intended physiological change in an animal, preferably a mammal. "Pharmaceutically acceptable additives" include cosolvents, surfactants, complexants, hydrotropes and other components that are desired for pharmaceutical use, as known in the art, such as pharmaceutically acceptable carriers, preservatives, emulsifying agents, diluents, sweeteners, flavorants, viscosity controlling agents, thickeners, colorants and melting agents. Any level of pharmaceutically acceptable additives and any individual pharmaceutically acceptable additive or combination of additives may be used, as long as these additives do not reduce the solubility below a desired level or make the composition toxic, as defined above. The term "pharmaceutically acceptable carrier" is known in the art, see, for example, U.S. Pat. No. 6,479,526. As used herein, "cosolvent" means a liquid or solid that mixes with water to form a solution of lower polarity than pure water. Examples of cosolvents are ethanol, ethylene glycol, glycerine, propylene glycol (PG), poly (ethylene glycol) and glycerol. Preferred concentrations of cosolvents are between 0.5 to 50 volume % and all individual values and ranges therein. As used herein, "surfactant" is a substance which can orient and accumulate at the water-air or water-organic interface and reduce the surface or interfacial tension. Examples of surfactants include Tween 20, Tween 80, sodium lauryl sulfate (SLS) and myristoyl camitine (MC). Preferred concentrations of surfactants are between 0.5 to 20 volume % and all individual values and ranges therein. As used herein, "complexant" means a substance which forms a molecular interaction with a solute having a definite stoichiometry (complex). The complex may be more soluble or less soluble than the pure solute. Most complexing agents that are used for solubilizing organic solutes in water are of the inclusion or stacking variety. Inclusion complexing agents can accept the solute into a cavity while stacking complexants form layered complexes. As used herein, "hydrotrope" means a substance which resembles a stacking complexing agent but which does not form a stoichiometric complex. Hydrotropes are a cross between a complexant and a surfactant. Examples of complexants include cyclodextrins (hydroxypropyl β-cyclodextrin, HPβCD, sulfobutyl ether β-cyclodextrin, SBEβCD), and other substituted alpha, beta, or gamma cyclodextrins and planar aromatic compounds which are water soluble such as benzoate and hydroxybenzoate salts, caffeine, and nicotinamide. Preferred concentrations of complexants and/or hydrotropes are between 0.5 to 40 volume % and all individual values and ranges therein. As used herein, "acidic buffer" means a compound or compounds that, when added to an aqueous solution, reduces the pH and causes the resulting solution to resist an increase in pH when the solution is mixed with solutions of higher pH. The acidic buffer must have a pKa below about 7. Some currently preferred ranges of pKa of the acidic buffer are below about 5, below about 4 and below about 3. Acidic buffers with all individual values and ranges of pKa below about 7 are included in the invention. Examples of acidic buffers are phosphate, citrate, acetate, succinate and combinations thereof. Suitable acidic buffers include acids and bases, as known in the art. One preferred acidic buffer is a combination of phosphoric acid and sugars that has a pH between 1 and 2. One composition is 10 mL of liquid contains 3.75 g fructose, and 3.75 g glucose, stabilized at pH 1.3 to 2.0 with orthophosphoric acid. One such combination is Emetrol® (Pharmacia & Upjohn Company Corporation, Kalamazoo, Mich.). Other examples include soft drink syrups. The pH of the composition formed from the weak base and acidic buffer and optional pharmaceutically acceptable additives must be below about 5 and all values and ranges therein. Some currently preferred ranges of pH of the resulting composition are below about 4, below about 3, below about 2, below about 1.5 and below about 1. As used herein, "about" is intended to indicate a range caused by experimental uncertainty. When used in conjunction with a pH, "about" means a value of ±0.5 pH units. When used in conjunction with a pKa, "about" means a value of ±0.5 pKa units.

BRIEF DESCRIPTION OF THE FIGURES

FIG. 3 shows the total solubility of carbendazim in cosolvent solutions at (A) pH 7.00, (B) pH 2.10.

FIG. 4 shows the total solubility of carbendazim in surfactant solutions at (A) pH 7.00, (B) pH 2.10.

FIG. 6 shows the total solubility of carbendazim in cosolvent solutions at (A) pH 7.00, (B) pH 1.95.

DETAILED DESCRIPTION OF THE INVENTION

The invention may be further understood by reference to the following non-limiting examples. One of ordinary skill in the art will appreciate that all weak bases other than those particularly exemplified can be used without undue experimentation.

Synthesis

Weak bases, including benzimidazole derivatives are commercially available or can be prepared in a number of ways well known to one skilled in the art of organic synthesis without undue experimentation. The benzimidazole derivatives are synthesized using the methods described below, together with synthetic methods known in the art of synthetic organic chemistry, or variations thereon as appreciated by those skilled in the art without undue experimentation. Each of the references cited below are hereby incorporated herein by reference.

Benzimidazole derivatives may be prepared according to the method described in U.S. Pat. No. 3,738,995 issued to Adams et al, Jun. 12, 1973. The thiazolyl derivatives may be prepared according to the method described in Brown et al., J. Am. Chem. Soc., 83 1764 (1961) and Grenda et al., J. Org. Chem., 30, 259 (1965).

Materials

Carbendazim was provided by the Procter & Gamble Company and used as received. Hydroxypropyl β-cyclodextrin (HPβCD) with an average molecular weight of 1390 and an average degree of substitution of 4.4 was obtained from Cyclodextrin Technologies Development Inc. (Gainesville, Fla.). Sulfobutyl ether β-cyclodextrin (SBEβCD) with an average molecular weight of 2160 and an average degree of substitution of 7 was a gift from Cydex, L. C. (Overland Park, Kans.). All other chemicals were of reagent grade, purchased from Sigma (St. Louis, Mo.) or Aldrich (St. Louis, Mo.) and used without further purification. Buffers were prepared according to the Henderson-Hasselbalch equation.

pH-Solubilization Profile

The buffer systems used for the pH-solubilization profile were 0.01 M sodium citrate/HCl with pH range 1.2–4.0, 0.01 M citrate-phosphate-borate/HCl with pH range 4.0–8.0, and 0.01M glycine/NaOH with pH range 8.0–12.0. In all the above mentioned buffers the ionic strength was maintained at 0.1M using sodium chloride. The effect of buffer species on the solubility of carbendazim at very low and high pH was not observed because the Ksp of each salt was not reached. Solubility at different pH was determined in the same manner as described below.

Solubility Determination

An excess amount of carbendazim was added to vials containing 2 ml of an aqueous solution of pH 2.00±0.15 and 7.00±0.15 at different concentrations (0, 1, 2.5, 5, and 10%) of cosolvents (EtOH, PG, PEG 400, and Glycerol), surfactants (Tween 20, Tween 80, sodium lauryl sulfate (SLS), and myristoyl camitine (MC)) and cyclodextrins (HPβCD and SBEβCD). In addition the cosolvents and cyclodextrins were studied at 20%. The sample vials were rotated at 20 rpm using an end-over-end mechanical rotator (Glas-Col Laboratory rotator, Terre Haute, Ind.) at ambient temperature for 10 days. Ten days was selected to ensure equilibrium because the strong crystal structure and high melting point (305° C.) (Budavari, S., 1996. The Merck Index, Twelfth ed. Merck & Co, New Jersey) of carbendazim contributes to a very slow dissolution rate. For solutions having pH greater than 9, the solubility was measured after 3 days rotation instead of 10 days because of the unstable nature of carbendazim in alkaline condition. The samples were filtered through a 0.45-μm filter and the pH at equilibrium was measured before performing HPLC analysis.

High Performance Liquid Chromatography (HPLC) Analysis

The HPLC assay used an Econosphere C8 column (150*4.6 mm, Alltech, Los Altos, Calif.) with a mobile phase composed of pure methanol. The flow rate was controlled at 1.0 ml/min (125 solvent Module, Beckman, Fullerton, Calif.) and the effluent was detected at 280 nm (168 detector, Beckman, Fullerton, Calif.). All experimental data are the average of duplicate values with an average error less than 3%.

Figure 1:
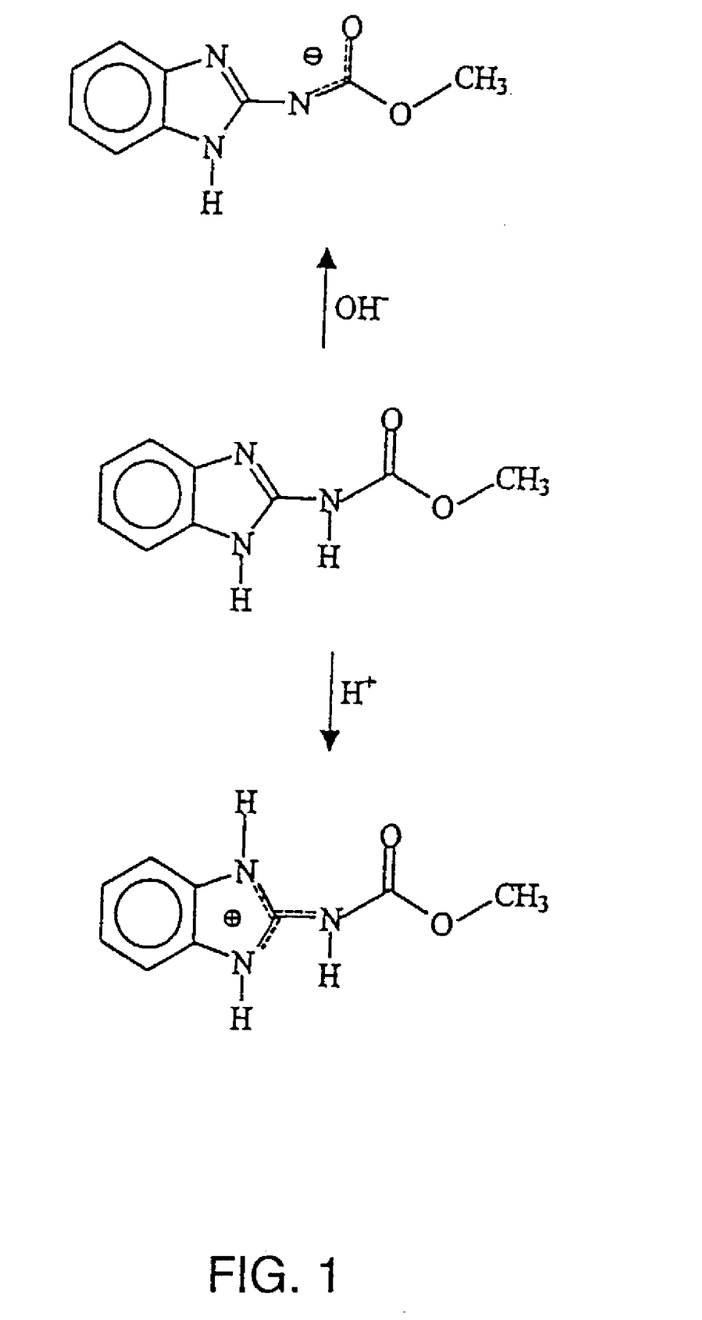
FIG. 1 shows the structure of carbendazim (methyl 2-benzimidazolecarbamate).
Figure 2:
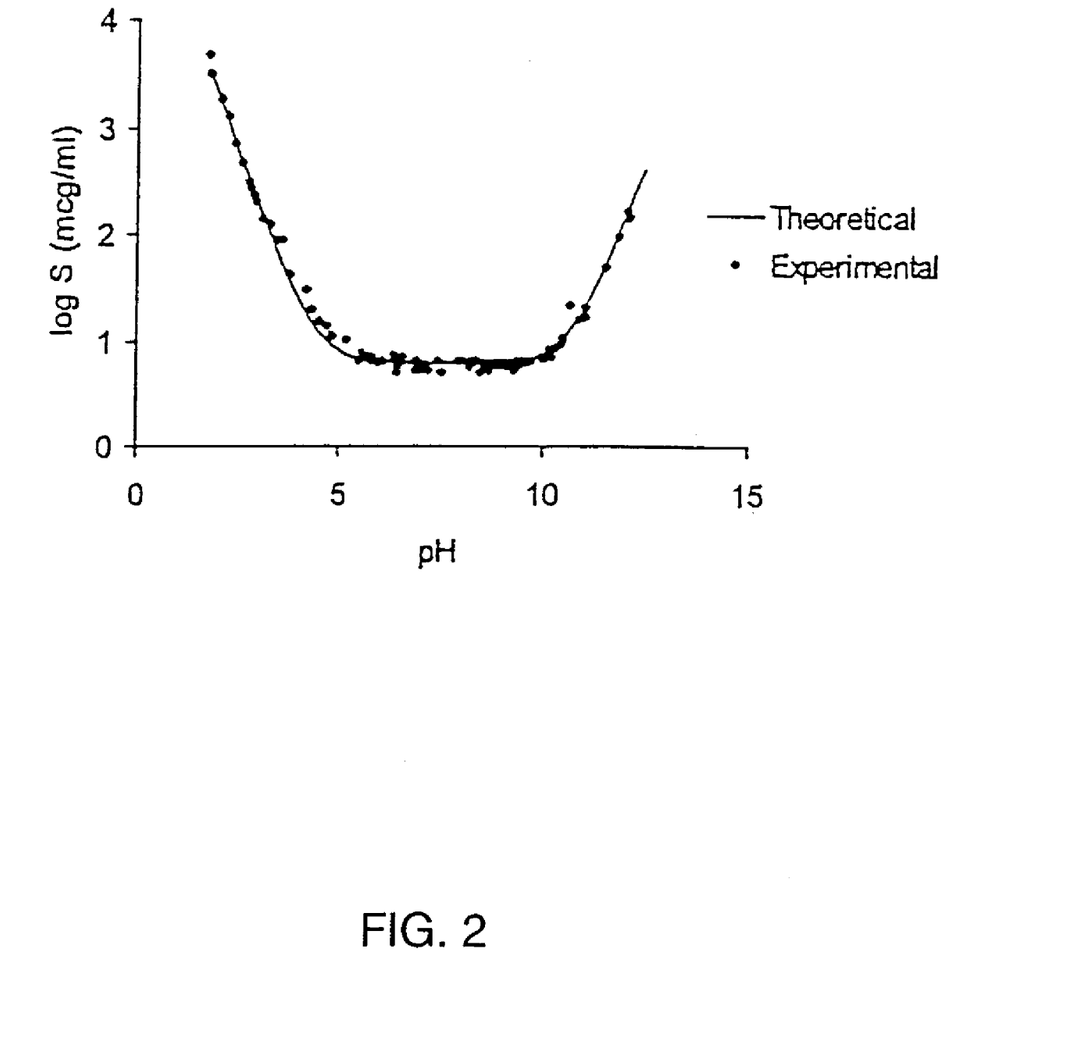
FIG. 2 shows the pH-solubilization profile of carbendazim.
Figure 7:
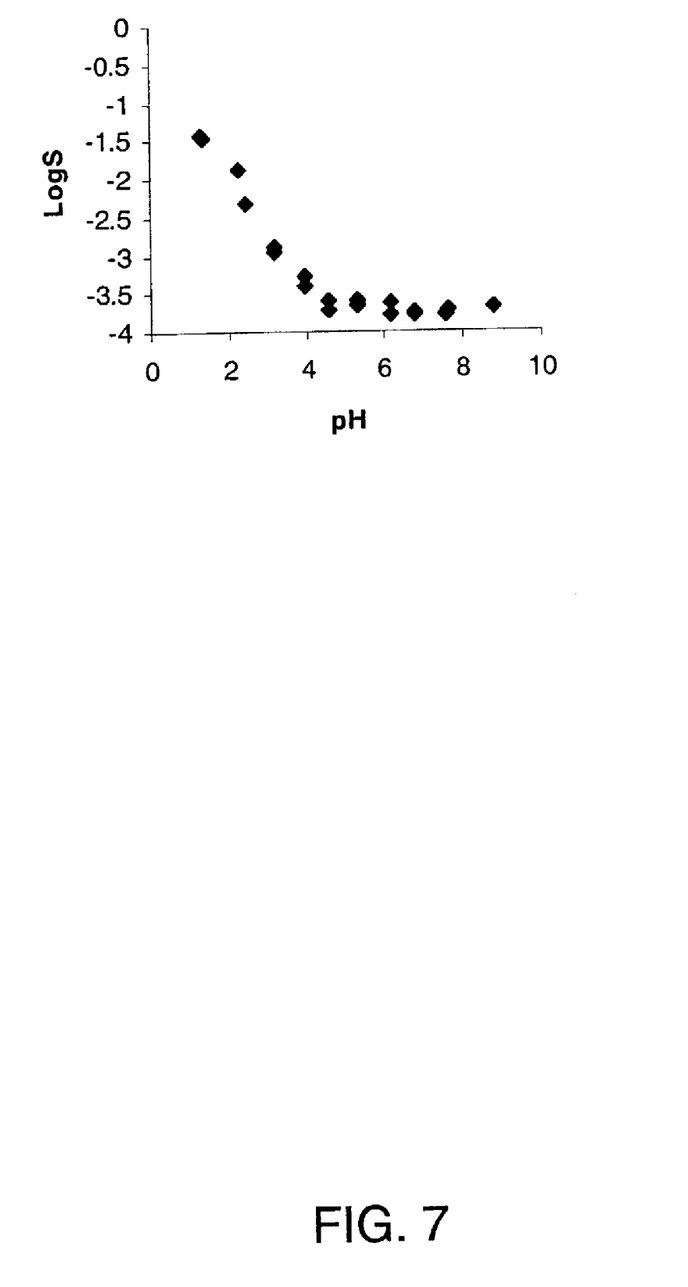
FIG. 7 shows the pH profile of the compound designated PG 300995.
Figure 8:
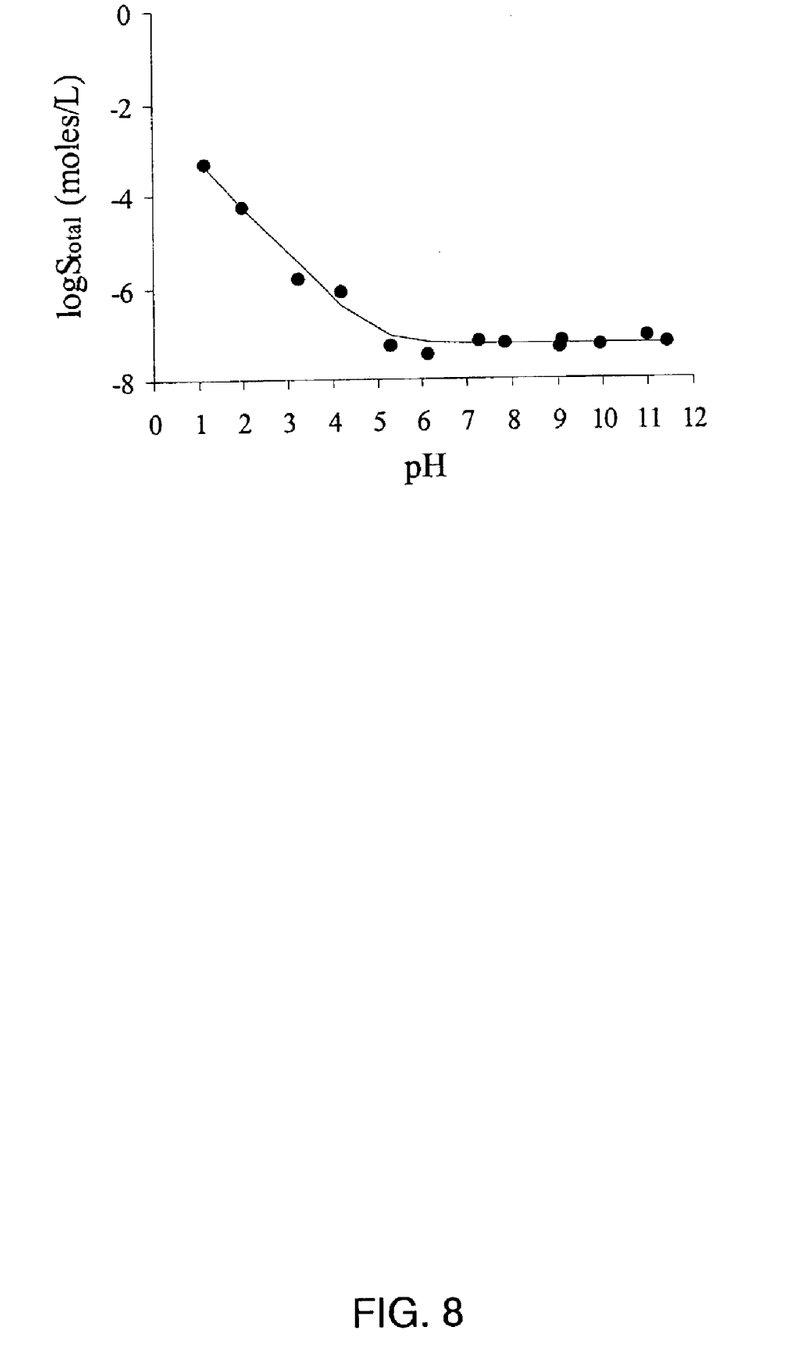
FIG. 8 shows the pH profile of the compound designated BPU NSC 639829.
Figure 9:
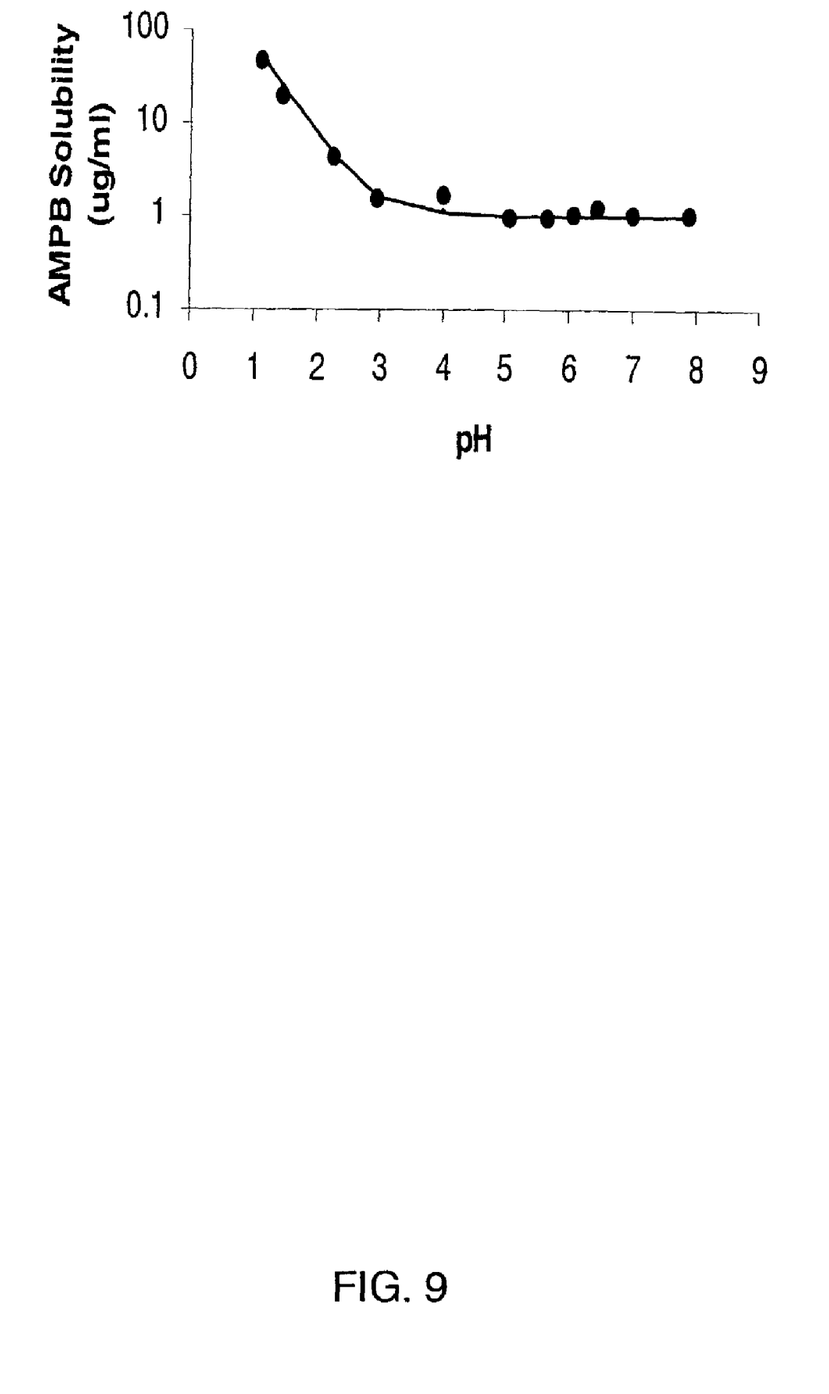
FIG. 9 shows the pH profile of the compound designated AMPB.

FIG. 1 shows the unionized and the ionized forms of carbendazim. The formation of a resonance-stabilized cation and anion is believed responsible for the high solubilities at low and high pH that are shown in FIG. 2. FIG. 2 shows that carbendazim has an intrinsic solubility of 6.11 μg/ml and its solubility increases with decreasing pH below 4.5 (the pKa of its basic guanadinium group), and with increasing pH above 10.6 (the pKa of its carbamide group). FIG. 2 also shows that the experimental pH-solubilization profile fits very well with the theoretical line calculated by the Henderson-Hasselbalch equation for an intrinsic solubility of 6.11 μg/ml, a basic pKa of 4.5 and an acidic pKa of 10.6. FIGS. 7–9 show the pH profile of three other drugs, obtained using analogous methods.

Figure 3A:
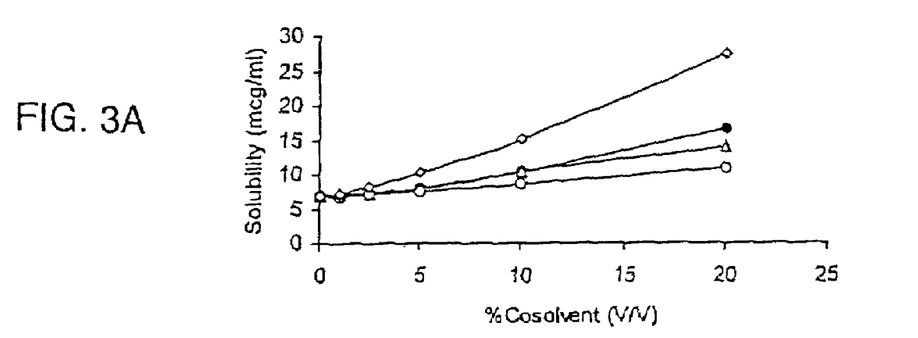

FIG. 3A shows the aqueous solubility of carbendazim versus the concentration of EtOH (filled circle), PG (triangle), PEG 400 (diamond), and Glycerol (open circle) at pH 7. In all cases there is an exponential increase in the solubility with increasing cosolvent concentration. The extent of solubilization depends both on the concentration and the polarity of cosolvents. The order of solubilization by four cosolvents is PEG 400>EtOH>PG>Glycerol.

Figure 3B:
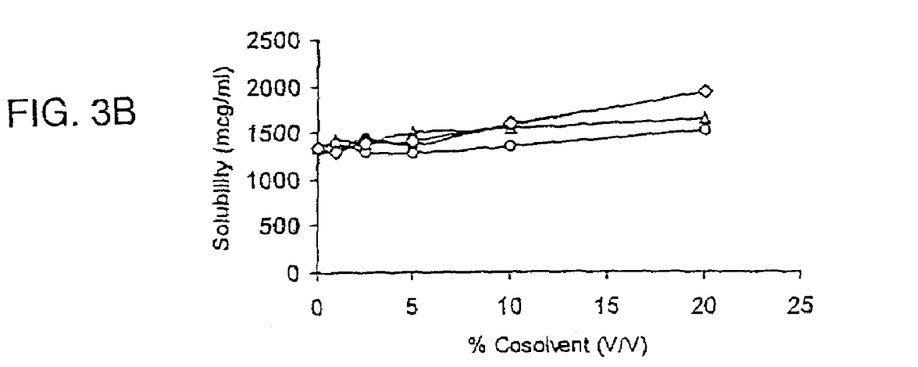

FIG. 3B shows the aqueous solubility of carbendazim versus the concentration of the same cosolvents at pH 2. From FIG. 3B, we can conclude that there is only a slight effect of cosolvent on the total drug solubility at pH 2, with the cosolvents following the same order as at pH 7. While the percentage increase is smaller at pH 2, the number of milligrams solubilized is larger.

Figure 4A:
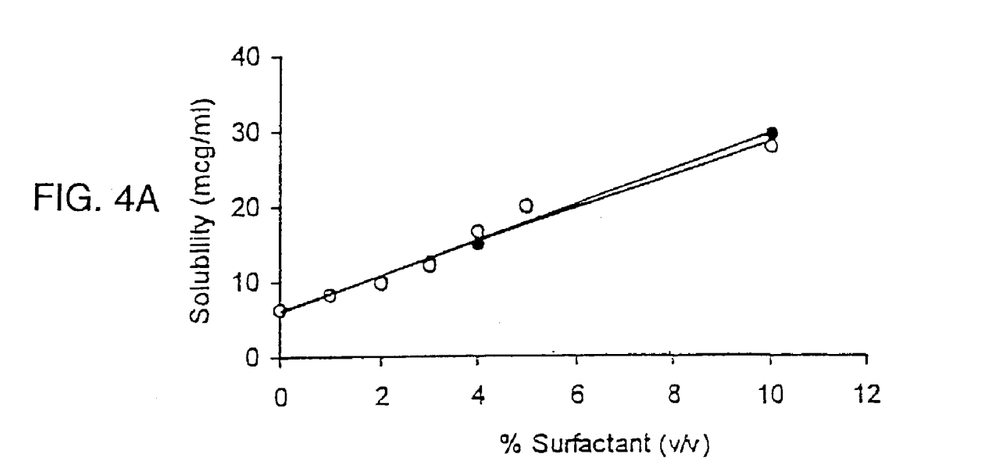
Figure 4B:
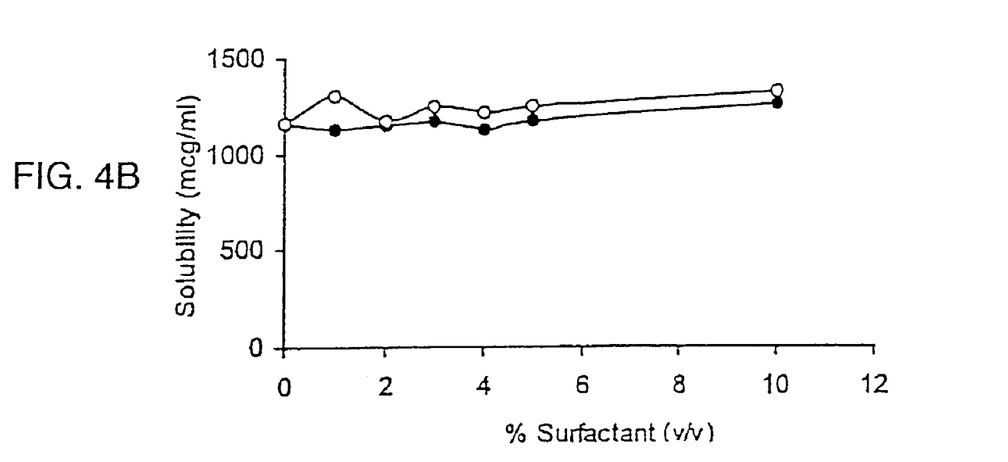

FIG. 4 shows the total solubility of carbendazim at pH 7 and 2, respectively, for different concentrations of Tween 20 (filled circle) and 80 (open circle) solutions. The critical micelle concentrations of Tween 20 and 80 are 0.006 and 0.0014%, respectively (Florence, A. T., Attwood, D., 1988. Physicochemical Principles of Pharmacy, Second ed. Chapman and Hall, New York) which is well below the minimum concentration of surfactant used for solubilization. At pH 7, the total drug solubility increases equally with increasing the concentration of either surfactant. On the other hand, there is no significant change in the total solubility with increasing the surfactant concentration at pH 2, because the polar cationic species does not partition into the nonpolar region of the micelle. Also at high concentrations of micelles (which do not form homogeneous aqueous solutions), the volume of free water is reduced. This reduces the amount of the ionized species in the free water. Therefore, the net effect of micellization on the total drug solubility is the result of the increase in the solubility of the unionized drug by the micelle, the decrease in the amount of the ionized drug in the free water, (i.e. the volume of the solution not occupied by the micelles), and the increase (if any) in the solubility of the ionized drug in the micelle.

FIG. 4 also shows that there is no significant difference on a weight basis between Tween 20 and 80 in solubilizing carbendazim at either pH 7 or 2. Solubilization at pH 2 is more efficient than solubilization at pH 7.

Figure 5:
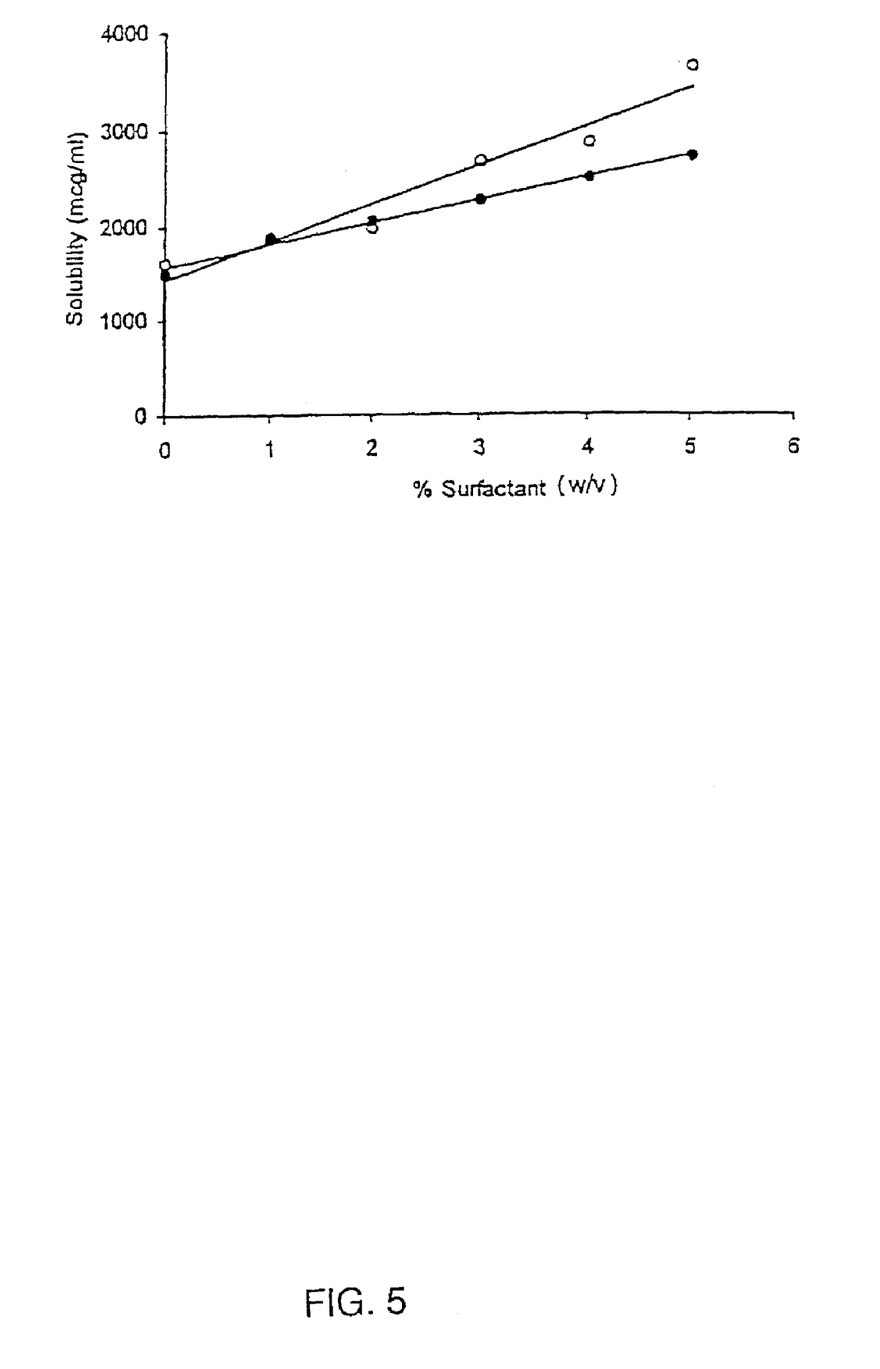
FIG. 5 shows the total solubility of carbendazim in surfactant solutions at pH 2.05; the filled circle indicates MC, the open circle indicates SLS.

Due to the high polarity of ionized carbendazim at pH 2, the ionic surfactants, sodium lauryl sulfate (SLS) and myristoyl carnitine (MC), were also studied at pH 2. FIG. 5 shows the total drug solubility of carbendazim at pH 2 for different concentrations of SLS (open circle) and MC (filled circle). These surfactants are also efficient solubilizers of the ionized drug at low pH.

Figure 6A:
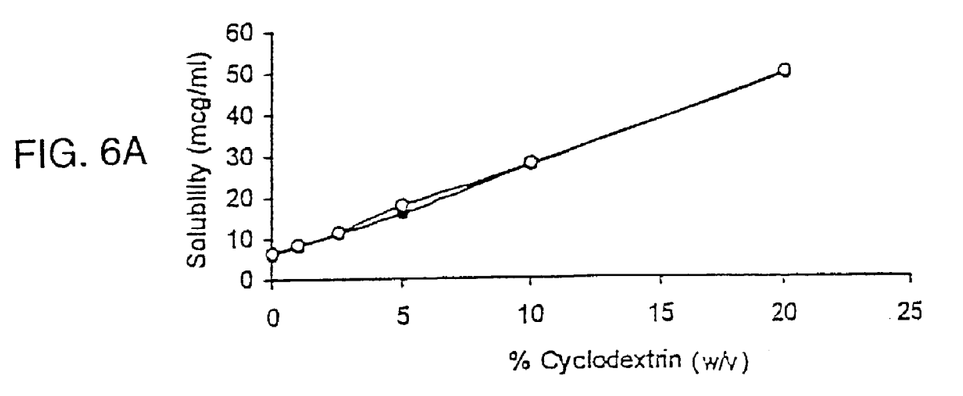
Figure 6B:
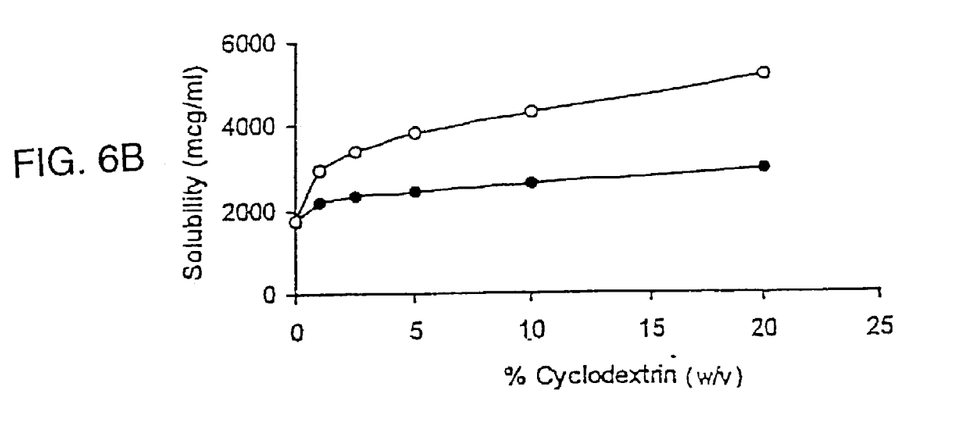

FIG. 6 shows that the total drug solubility increases both at pH 7 and 2 for HPβCD (filled circle) and SBEβCD (open circle). This suggests the formation of an inclusion complex between β-cyclodextrin and the benzene ring of drug molecule even though a large polar group is attached to the benzene ring when the drug is ionized at pH 2. FIG. 6A shows that both HPβCD and SBEβCD have the same capacity to solubilize unionized carbendazim at pH 7. On the other hand, FIG. 6B shows that SBEβCD increases the solubility more than HPβCD at pH 2, because the resultant complex is stabilized by the interaction between the anionic cyclodextrin and the cationic drug.

Formulations of benzimidazole derivatives for drug use include those discussed herein, as well as other formulations (compositions) that include components that increase the water solubility of benzimidazole derivatives and may include other components known in the pharmaceutical arts, such as those described above. One such component is an acid-sugar solution such as Emetrol® (Pharmacia & Upjohn Company Corporation, Kalamazoo, Mich.) (an anti nausea liquid) available over the counter. It is a solution of phosphoric acid and sugars with a pH between 1 and 2 that is an excellent vehicle for carbendazim and other weak bases. Such acid-sugar solutions can be given to humans orally in 15–30 ml doses, five times in an hour, four times a day. This amounts to a maximum daily dose of 600 ml. Since the solubility of carbendazim at pH 1 and 2 are 16 and 1.6 mg/ml, up to 100 mg carbendazim can be given orally in 100 ml of the vehicle. Soft drink syrups (with or without sweetening agents) and other acidic solutions suitable for consumption by mammals can also be used as vehicles for oral formulations.

Since an oral formulation is typically administered along with a fluid like water or juice it is essential to study the effect of dilution of the formulation with these fluids. This can be investigated by a simple serial dilution precipitation study, for example, serial dilutions of the formulation with equal volumes of Seven Up, water, and pH 7 buffer.

0.1 ml formulation was added to a test tube containing 1, 10, or 25 ml each of soda solution (Seven Up), 0.01M pH 7 phosphate buffer solution, or water. The mixed solution was shaken by hand for 5 seconds. The presence or absence of carbendazim crystal was determined visually and the final pH was recorded. The visual determination of the carbendazim crystals was also performed at one day later after dilution.

TABLE 1

Precipitation results for oral formulations

| Formulation | Dose(mg/ml) | Dilution with Vehicle Ratio pH | Seven Up (3.26) | | | Water (5.50) | | | pH 7 Buffer | | |
|---|---|---|---|---|---|---|---|---|---|---|---|
| | | | 1:10 3.01 | 1:100 3.18 | 1:250 3.22 | 1:10 3.00 | 1:100 3.75 | 1:250 4.15 | 1:10 6.50 | 1:100 6.96 | 1:250 6.97 |
| pH 2 Buffer | 1 | Initial | – | – | – | – | – | – | + | – | – |
| | | 1 day | – | – | – | – | – | – | + | – | – |
| 5% MCpH 2 | 2 | Initial | – | – | – | – | – | – | + | – | – |
| | | 1 day | – | – | – | – | – | – | + | – | – |

(+): precipitation;
(–): no precipitation

TABLE 2

Summary of solubility of carbendazim in different vehicles

| | Solubility of carbendazim (mg/ml) | |
|---|---|---|
| Vehicle | Unionized (pH 7.00 ± 0.15) | Ionized (pH 2.00 ± 0.15) |
| Buffered solution | 0.006 | 1.64 |
| 20% Ethanol | 0.016 | 1.94 |
| 20% PG | 0.014 | 1.66 |
| 20% Glycerine | 0.010 | 1.52 |
| 20% PEG 400 | 0.027 | 1.93 |
| 10% Tween 20 | 0.030 | 1.26 |
| 10% Tween 80 | 0.028 | 1.33 |
| 5% SLS | N/A | 3.66 |
| 5% MC | N/A | 2.73 |
| 20% HPβCD | 0.049 | 2.96 |
| 20% SBEβCD | 0.050 | 5.20 |

Table 1 shows the result of a precipitation study for two oral formulations, 1 mg/ml carbendazim buffered solution at pH 2 and 2 mg/ml carbendazim in 5% buffered MC solution at pH 2. It is evident from Table 1 that both above formulations did not precipitate in Seven Up and water at dilutions varying from 10 to 250 times. The final pHs of the diluted solutions were also measured and listed in Table 1. When the formulation is diluted to the point at which the concentration of hydrogen ion or hydroxide ion is not sufficient to maintain the solubility of the drug above the concentration present, precipitation will occur. Therefore, soda and water can be used efficiently to administer the above formulations orally. The dramatic shift in the pH of the formulations from 2 to 6.9 is responsible for the precipitation when diluted with pH 7 buffer solution by 1:10 ratio. However, when diluted 100 and 250 times with pH 7 buffer solution no precipitation is observed visually. On observation under the microscope, the formulations diluted 100 times did show some small crystals of the drug.

Table 2 summarizes the solubility of carbendazim in different vehicles at pH 7 and pH2.

Mouse Study

Figure 10:
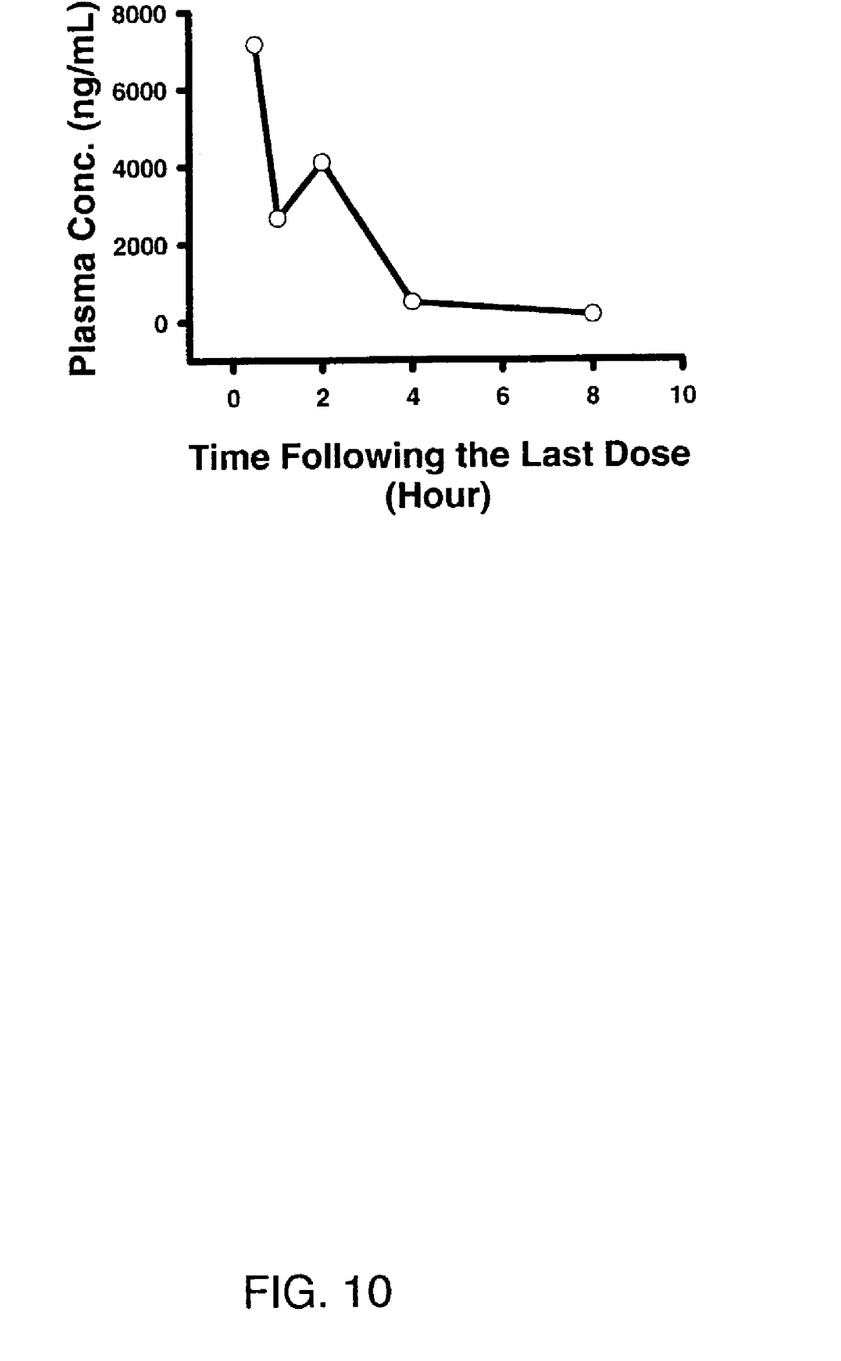
FIG. 10 shows the plasma concentration of carbendazim as a function of time.

The bioavailability of carbendazim was studied in the mouse. An intravenous dose, a formulation of carbendazim in corn oil, and a formulation of carbendazim in phosphoric acid corresponding to the phosphoric acid concentration in Emetrol were each given to a mouse. The blood levels versus time profile of the Emetrol formulation is shown in FIG. 10. The blood level on the graph is indicative of the amount of drug absorbed divided by the blood volume of the mouse. The 75% bioavailability of carbendazim from the Emetrol formulation is more than ten times greater than that of the corn oil formulation

TABLE 3

| Route | Formulation | Dose | Cmax (mg/mL) | % Bioavailability |
|---|---|---|---|---|
| IV | — | 6.4 μg | 15 | 100% |
| PO (by mouth) | Corn oil | 132.0 mg | 15–20 | 4.8–6.4% |
| PO (by mouth) | Emetrol | 4.7 mg | 7 | 75% |

Although the description above contains many specificities, these should not be construed as limiting the scope of the invention, but as merely providing illustrations of some of the presently preferred embodiments of the invention. For example, pharmaceutically acceptable additives other than those specifically mentioned may be used to improve the water solubility of the weak bases. In addition, weak bases other than those specifically exemplified may be used without undue experimentation using the guidance presented herewith. All references cited herein are incorporated by reference to the extent not inconsistent with the disclosure herewith.

I claim:

1. A pharmaceutical composition comprising:
a benzimidazole compound having a pKa below about 7 and having the formula:

wherein X is hydrogen, halogen, alkyl of less than 7 carbon atoms or alkoxy of less than 7 carbon atoms; n is a positive integer of less than 4; Y is hydrogen, chlorine, nitro, methyl, ethyl or oxychloro; R is hydrogen, alkylaminocarbonyl wherein the alkyl group has from 3 to 6 carbon atoms or an alkyl group having from 1 to 8 carbons, and $R_2$ is 4-thiazolyl, NHCOOR$_1$ wherein $R_1$ is an aliphatic hydrocarbon of less than 7 carbon atoms, or an alkyl group of less than 7 carbon atoms; or a compound of formula:

where n is an integer from 1 to 3 and R is hydrogen, alkyl having from 1 to 7 carbon atoms, chloro, bromo, fluoro, oxychloro, hydroxy, sulfhydryl or alkoxy having the formula —O(CH$_2$)$_y$CH$_3$ wherein y is an integer from 0 to 6;

its pharmaceutically acceptable salt or its conventional prodrug of the hydroxy, amine or sulfhydryl group; an aqueous buffer solution of phosphoric acid and sugar with a pH between 1 and 2; and optionally pharmaceutically acceptable additives, wherein the composition has a pH below about 4.

2. The pharmaceutical composition of claim 1, wherein the composition is administered orally.

3. The pharmaceutical composition of claim 1, wherein the composition has a pH below about 3.

4. The pharmaceutical composition of claim 1, wherein the compound has a compound pKa below 5.

5. The pharmaceutical composition of claim 1, wherein the compound has a compound pKa below 4.

6. The pharmaceutical composition of claim 3, wherein the buffer has a buffer pKa below 5.

7. The pharmaceutical composition of claim 3, wherein the buffer has a buffer pKa below 3.

8. The pharmaceutical composition of claim 1, wherein the compound is:

where n is an integer from 1 to 3 and R is hydrogen, alkyl having from 1 to 7 carbon atoms, chloro, bromo, fluoro, oxychloro, hydroxy, sulfhydryl or alkoxy having the formula —O(CH$_2$)$_y$CH$_3$ wherein y is an integer from 0 to 6.

9. The composition of claim 1, wherein R is H.

10. The composition of claim 1, wherein the benzimidazole compound is

11. The composition of claim 1, wherein the composition consists essentially of:

a benzimidazole compound having a pKa below about 7 and having the formula:

wherein X is hydrogen, halogen, alkyl of less than 7 carbon atoms or alkoxy of less than 7 carbon atoms; n is a positive integer of less than 4; Y is hydrogen, chlorine, nitro, methyl, ethyl or oxychloro; R is hydrogen, alkylaminocarbonyl wherein the alkyl group has from 3 to 6 carbon atoms or an alkyl group having from 1 to 8 carbons, and R$_2$ is 4-thiazolyl, NHCOOR$_1$ wherein R$_1$ is an aliphatic hydrocarbon of less than 7 carbon atoms, or an alkyl group of less than 7 carbon atoms; or a compound of formula:

where n is an integer from 1 to 3 and R is hydrogen, alkyl having from 1 to 7 carbon atoms, chloro, bromo, fluoro, oxychloro, hydroxy, sulfhydryl or alkoxy having the formula —O(CH$_2$)$_y$CH$_3$ wherein y is an integer from 0 to 6;

an acidic buffer having a buffer pKa below about 7; and optional pharmaceutically acceptable additives, wherein the composition has a ph below about 4.

12. The composition of claim 1, wherein the composition consists essentially of: a benzimidazole compound having a pKa below about 7 and having the formula:

wherein X is hydrogen, halogen, alkyl of less than 7 carbon atoms or alkoxy of less than 7 carbon atoms; n is a positive integer of less than 4; Y is hydrogen, chlorine, nitro, methyl, ethyl or oxychloro; R is hydrogen, alkylaminocarbonyl wherein the alkyl group has from 3 to 6 carbon atoms or an alkyl group having from 1 to 8 carbons, and R$_2$ is 4-thiazolyl, NHCOOR$_1$ wherein R$_1$ is an aliphatic hydrocarbon of less than 7 carbon atoms, or an alkyl group of less than 7 carbon atoms; or a compound of formula:

where n is an integer from 1 to 3 and R is hydrogen, alkyl having from 1 to 7 carbon atoms, chloro, bromo, fluoro, oxychloro, hydroxy, sulfhydryl or alkoxy having the formula —O(CH$_2$)$_y$CH$_3$ wherein y is an integer from 0 to 6; and an acidic buffer having a buffer pKa below about7.

13. The composition of claim 1, further comprising water.

14. The composition of claim 1, wherein the benzimidazole compound has the formula:

wherein R is hydrogen or an alkyl of 1 through 8 carbon atoms and R$_2$ is selected from the group consisting of 4-thiazolyl, or NHCOOR$_1$ wherein R$_1$ is methyl, ethyl or isopropyl.

15. The composition of claim 14, wherein R is H.

16. A pharmaceutical composition comprising:

(a) a benzimidazole compound having the formula:

wherein X is hydrogen, halogen, alkyl of less than 7 carbon atoms or alkoxy of less than 7 carbon atoms; n is a positive integer of less than 4; Y is hydrogen, chlorine, nitro, methyl, ethyl or oxychloro; R is hydrogen, alkylaminocarbonyl wherein the alkyl group has from 3 to 6 carbon atoms or an alkyl group having from 1 to 8 carbons and R$_2$ is 4-thiazolyl, NHCOOR$_1$ wherein R$_1$ is aliphatic hydrocarbon of less than 7 carbon atoms, or an alkyl group of less than 7 carbon atoms; or a compound of formula:

where n is an integer from 1 to 3 and R is hydrogen, alkyl having from 1 to 7 carbon atoms, chloro, bromo, fluoro, oxychloro, hydroxy, sulfhydryl or alkoxy having the formula —O(CH$_2$)$_y$CH$_3$ wherein y is an integer from 0 to 6;

(b) a pharmaceutically acceptable carrier; and (c) an aqueous acidic buffer solution of phosphoric acid and sugar with a pH between 1 and 2.

17. The composition of claim 16, wherein the benzimidazole compound is carbendazim.

18. The composition of claim 16, wherein the composition has a pH below about 3.

19. The composition of claim 16, wherein the benzimidazole compound has the formula:

wherein R is an alkyl of 1 through 8 carbon atoms and $R_2$ is selected from the group consisting of 4-thiazolyl, NHCOOR$_1$ wherein $R_1$ is methyl, ethyl or isopropyl.

20. A composition comprising:
a compound of formula wherein X is hydrogen, halogen, alkyl of less than 7 carbon atoms or alkoxy of less than 7 carbon atoms; n is a positive integer of less than 4; Y is hydrogen, chlorine, nitro, methyl, ethyl or oxychloro; R is hydrogen, alkylaminocarbonyl wherein the alkyl group has from 3 to 6 carbon atoms or an alkyl group having from 1 to 8 carbons and $R_2$ is 4-thiazolyl, NHCOOR$_1$ wherein $R_1$ is an aliphatic hydrocarbon of less than 7 carbon atoms, or an alkyl group of less than 7 carbon atoms; or a compound of formula:

where n is an integer from 1 to 3 and R is hydrogen, alkyl having from 1 to 7 carbon atoms, chloro, bromo, fluoro, oxychloro, hydroxy, sulfhydryl or alkoxy having the formula —O(CH$_2$)$_y$CH$_3$ wherein y is an integer from 0 to 6 having a compound pKa below about 7;
an aqueous acidic buffer solution of phosphoric acid and sugar with a pH between 1 and 2; and
optional pharmaceutically acceptable additives, wherein the composition has a pH below about 4.

21. A method of increasing the water solubility of a compound of formula wherein X is hydrogen, halogen, alkyl of less than 7 carbon atoms or alkoxy of less than 7 carbon atoms; n is a positive integer of less than 4; Y is hydrogen, chlorine, nitro, methyl, ethyl or oxychloro; R is hydrogen, alkylaminocarbonyl wherein the alkyl group has from 3 to 6 carbon atoms or an alkyl group having from 1 to 8 carbons and $R_2$ is 4-thiazolyl, NHCOOR$_1$ wherein $R_1$ is an aliphatic hydrocarbon of less than 7 carbon atoms, or an alkyl group of less than 7 carbon atoms; or a compound of formula:

where n is an integer from 1 to 3 and R is hydrogen, alkyl having from 1 to 7 carbon atoms, chloro, bromo, fluoro, oxychloro, hydroxy, sulfhydryl or alkoxy having the formula —O(CH$_2$)$_y$CH$_3$ wherein y is an integer from 0 to 6 having a compound pKa below about 7, comprising contacting said compound with an aqueous acidic buffer solution of phosphoric acid and sugar with a pH between 1 and 2, forming a composition, and optionally adding pharmaceutically acceptable additives, wherein the composition has a pH below about 4.

22. The method of claim 21, wherein the compound is carbendazim.

23. The method of claim 21, wherein the pH of the composition is below 3.

24. The method of claim 21, wherein the composition further comprises water.

* * * * *